United States Patent
Groene et al.

(10) Patent No.: US 11,684,384 B2
(45) Date of Patent: Jun. 27, 2023

(54) RESTRICTED USAGE FEATURES FOR SURGICAL INSTRUMENT

(71) Applicant: Cilag GmbH International, Zug (CH)

(72) Inventors: David C. Groene, Cincinnati, OH (US); Benjamin J. Danziger, Kenmore, WA (US)

(73) Assignee: Cilag GmbH International, Zug (CH)

(*) Notice: Subject to any disclaimer, the term of this patent is extended or adjusted under 35 U.S.C. 154(b) by 615 days.

(21) Appl. No.: 16/779,759

(22) Filed: Feb. 3, 2020

(65) Prior Publication Data
US 2020/0237398 A1     Jul. 30, 2020

Related U.S. Application Data

(63) Continuation of application No. 14/951,670, filed on Nov. 25, 2015, now Pat. No. 10,639,059.

(51) Int. Cl.
| | |
|---|---|
| *A61B 17/32* | (2006.01) |
| *A61B 17/00* | (2006.01) |
| *A61B 90/00* | (2016.01) |

(52) U.S. Cl.
CPC .......... *A61B 17/320092* (2013.01); *A61B 2017/00482* (2013.01); *A61B 2017/00486* (2013.01); *A61B 2017/320069* (2017.08); *A61B 2017/320071* (2017.08); *A61B 2017/320089* (2017.08); *A61B 2017/320094* (2017.08); *A61B 2017/320095* (2017.08); *A61B 2090/0803* (2016.02); *A61B 2090/0807* (2016.02); *A61B 2090/0814* (2016.02)

(58) Field of Classification Search
CPC ...... A61B 17/320092; A61B 17/00486; A61B 2017/00486; A61B 2090/0803; A61B 2090/0807; A61B 2090/0814
See application file for complete search history.

(56) References Cited

U.S. PATENT DOCUMENTS

| | | |
|---|---|---|
| 5,322,055 A | 6/1994 | Davison et al. |
| 5,400,267 A | 3/1995 | Denen et al. |
| 5,873,873 A | 2/1999 | Smith et al. |

(Continued)

FOREIGN PATENT DOCUMENTS

| | | |
|---|---|---|
| EP | 2 641 552 A2 | 9/2013 |
| WO | WO 98/06338 A2 | 2/1998 |
| WO | WO 2013/102058 A1 | 7/2013 |

OTHER PUBLICATIONS

European Examination Report dated Dec. 5, 2019 for Application No. EP 16805627.3, 6 pgs.

(Continued)

*Primary Examiner* — Sarah A Simpson
(74) *Attorney, Agent, or Firm* — Frost Brown Todd LLP

(57) ABSTRACT

Systems, devices and methods for managing surgical instruments throughout their lifecycle include disabling a usage based device lockout and providing notifications for devices nearing a usage based lockout. A device adaptor connected inline between a surgical instrument and a power source can be configured to alter a device EEPROM to allow for additional device usage despite a usage based lockout. Notifications and user prompts may be displayed requiring a user to acknowledge that a usage based device lockout has occurred in order to avoid an attempt to use an expired device in a future procedure.

20 Claims, 8 Drawing Sheets

(56) References Cited

U.S. PATENT DOCUMENTS

| | | | |
|---|---|---|---|
| 5,980,510 | A | 11/1999 | Tsonton et al. |
| 6,325,811 | B1 | 12/2001 | Messerly |
| 6,338,657 | B1 | 1/2002 | Harper et al. |
| 6,773,444 | B2 | 8/2004 | Messerly |
| 6,783,524 | B2 | 8/2004 | Anderson et al. |
| 8,461,744 | B2 | 6/2013 | Wiener et al. |
| 8,591,536 | B2 | 11/2013 | Robertson |
| 8,623,027 | B2 | 1/2014 | Price et al. |
| 8,986,302 | B2 | 3/2015 | Aldridge et al. |
| 9,023,071 | B2 | 5/2015 | Miller et al. |
| 9,095,367 | B2 | 8/2015 | Olson et al. |
| 9,393,037 | B2 | 7/2016 | Olson et al. |
| 9,402,647 | B2 | 8/2016 | Kawashima et al. |
| 2006/0079874 | A1 | 4/2006 | Faller et al. |
| 2006/0161054 | A1* | 7/2006 | Reuss ..................... A61B 5/00 600/338 |
| 2007/0191713 | A1 | 8/2007 | Eichmann et al. |
| 2007/0282333 | A1 | 12/2007 | Fortson et al. |
| 2008/0200940 | A1 | 8/2008 | Eichmann et al. |
| 2011/0087212 | A1* | 4/2011 | Aldridge ............ A61B 18/1206 606/34 |
| 2015/0272580 | A1 | 10/2015 | Leimbach et al. |

OTHER PUBLICATIONS

European Search Report, Extended, and Written Opinion dated Dec. 6, 2019 for Application No. EP 19205842.8, 8 pgs.
International Search Report and Written Opinion dated Apr. 6, 2017 for Application No. PCT/US2016/062003, 17 pgs.

* cited by examiner

RESTRICTED USAGE FEATURES FOR SURGICAL INSTRUMENT

PRIORITY

This application is a continuation of U.S. patent application Ser. No. 14/951,670, entitled "Restricted Usage Features for Surgical Instrument," filed Nov. 25, 2015, and published as U.S. Pat. Pub. 2017/0143366 on May 25, 2017, issued as U.S. Pat. No. 10,639,059 on May 5, 2020, the entire disclosure of which is incorporated by reference herein.

BACKGROUND

A variety of surgical instruments include an end effector having a blade element that vibrates at ultrasonic frequencies to cut and/or seal tissue (e.g., by denaturing proteins in tissue cells). These instruments include piezoelectric elements that convert electrical power into ultrasonic vibrations, which are communicated along an acoustic waveguide to the blade element. The precision of cutting and coagulation may be controlled by the surgeon's technique and adjusting the power level, blade edge, tissue traction and blade pressure.

Examples of ultrasonic surgical instruments include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," filed Oct. 10, 1997, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; and U.S. Pat. No. 6,783,524, entitled "Robotic Surgical Tool with Ultrasound Cauterizing and Cutting Instrument," issued Aug. 31, 2004, the disclosure of which is incorporated by reference herein.

Still further examples of ultrasonic surgical instruments are disclosed in U.S. Pub. No. 2006/0079874, entitled "Tissue Pad for Use with an Ultrasonic Surgical Instrument," published Apr. 13, 2006, now abandoned, the disclosure of which is incorporated by reference herein; U.S. Pub. No. 2007/0191713, entitled "Ultrasonic Device for Cutting and Coagulating," published Aug. 16, 2007, now abandoned, the disclosure of which is incorporated by reference herein; U.S. Pub. No. 2007/0282333, entitled "Ultrasonic Waveguide and Blade," published Dec. 6, 2007, now abandoned, the disclosure of which is incorporated by reference herein; U.S. Pub. No. 2008/0200940, entitled "Ultrasonic Device for Cutting and Coagulating," published Aug. 21, 2008, now abandoned, the disclosure of which is incorporated by reference herein; U.S. Pub. No. 2009/0105750, entitled "Ergonomic Surgical Instruments," published Apr. 23, 2009, issued as U.S. Pat. No. 8,623,027 on Jan. 7, 2014, the disclosure of which is incorporated by reference herein; U.S. Pub. No. 2010/0069940, entitled "Ultrasonic Device for Fingertip Control," published Mar. 18, 2010, issued as U.S. Pat. No. 9,023,071, on May 5, 2015, the disclosure of which is incorporated by reference herein; and U.S. Pub. No. 2011/0015660, entitled "Rotating Transducer Mount for Ultrasonic Surgical Instruments," published Jan. 20, 2011, issued as U.S. Pat. No. 8,461,744 on Jun. 11, 2013, the disclosure of which is incorporated by reference herein; and U.S. Pub. No. 2012/0029546, entitled "Ultrasonic Surgical Instrument Blades," published Feb. 2, 2012, issued as U.S. Pat. No. 8,591,536 on Nov. 26, 2013, the disclosure of which is incorporated by reference herein.

Some ultrasonic surgical instruments may include an articulating shaft section. Examples of such ultrasonic surgical instruments are disclosed in U.S. Pub. No. 2014/0005701, entitled "Surgical Instruments with Articulating Shafts," published Jan. 2, 2014, issued as U.S. Pat. No. 9,393,037 on Jul. 19, 2016, the disclosure of which is incorporated by reference herein; and U.S. Pub. No. 2014/0114334, entitled "Flexible Harmonic Waveguides/Blades for Surgical Instruments," published Apr. 24, 2014, issued as U.S. Pat. No. 9,095,367 on Aug. 4, 2015, the disclosure of which is incorporated by reference herein.

As a result of the critical nature of procedures performed with surgical instruments, extremely tight tolerances may be required both for newly manufactured instruments as well as for reusable instruments that have previously been put into service. While a particular surgical instrument may meet or exceed a specification at the time of manufacture, its performance may degrade after several uses due to normal wear and tear, or due to expansion of parts as a result of heat sterilization between uses. While manufacturers of such a product my provide guidelines for a number of uses before an instrument should be disposed, cost conscious end users may ignore such guidelines and create safety and usage issues for end users and patients.

While a variety of systems have been made and used for surgical device lifecycle management, it is believed that no one prior to the inventor(s) has made or used the technology as described herein.

BRIEF DESCRIPTION OF THE DRAWINGS

It is believed the present invention will be better understood from the following description of certain examples taken in conjunction with the accompanying drawings, in which like reference numerals identify the same elements and in which.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument.

I. Overview of Exemplary Ultrasonic Surgical Instruments

Figure 1:
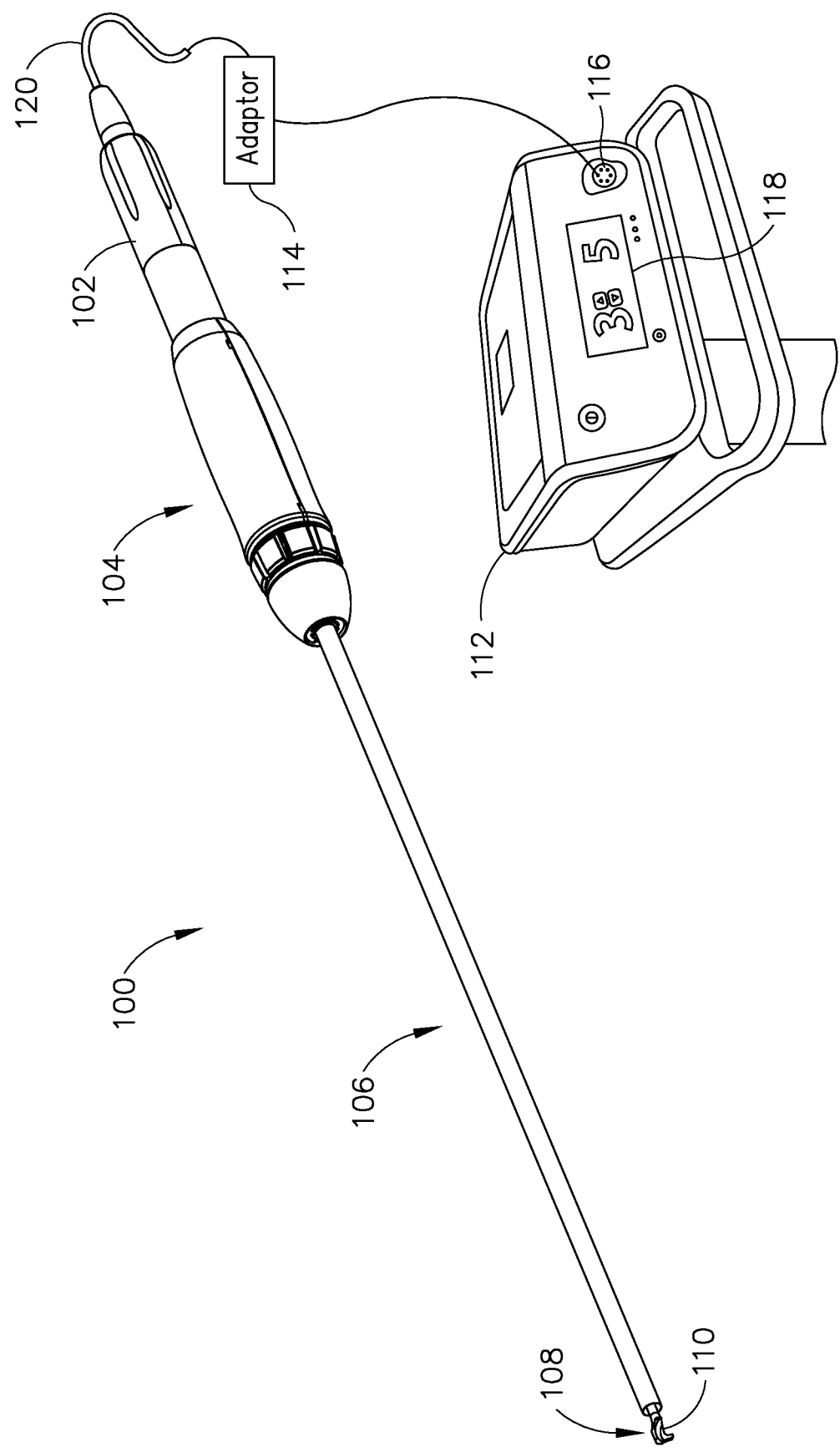
FIG. 1 depicts a perspective view of a first exemplary surgical instrument.

Turning now to the figures, FIG. 1 shows a perspective view of an exemplary surgical instrument (100). As described therein and as will be described in greater detail below, instrument (100) is operable to cut tissue and seal or weld tissue substantially simultaneously. It should also be understood that instrument (100) may have various structural and functional similarities with the HARMONIC SYNERGY® Ultrasonic Instrument. Furthermore, instrument (100) may have various structural and functional similarities with the devices taught in any of the other references that are cited and incorporated by reference herein.

Instrument (100) is configured to be used as a scalpel. As shown in FIG. 1, instrument (100) of this example comprises a handle assembly (104), a shaft assembly (106), and an end effector (108). The proximal end of instrument (100) receives and is fitted with an ultrasonic transducer assembly (102) by insertion of ultrasonic transducer assembly (102) into handle assembly (104). Handle assembly (104) is configured to receive ultrasonic transducer assembly (102) such that ultrasonic transducer assembly (102) may be coupled to an acoustic waveguide (not shown) in shaft assembly (106) by a threaded connection, though any other suitable type of coupling may be used. As shown in FIG. 1, instrument (100) may be coupled with ultrasonic transducer assembly (102) to form a single unit. Ultrasonic transducer assembly (102) includes a set of piezoelectric elements (not shown) that are located proximal to a horn (not shown) of the rigid acoustic waveguide. The piezoelectric discs are operable to convert electrical power into ultrasonic vibrations, which are then transmitted along acoustic waveguide, which extends through shaft assembly (106), to a blade (110) of end effector (108) in accordance with known configurations and techniques. By way of example only, this portion of the acoustic drivetrain may be configured in accordance with various teachings of various references that are cited herein.

Blade (110) may be integral with the acoustic waveguide (not shown) and formed as a single unit. In some versions, blade (110) may be connected to a waveguide by a threaded connection, a welded joint, and/or some other coupling feature(s). The distal end of blade (110) is disposed at or near a longitudinal position corresponding to an anti-node associated with ultrasonic vibrations communicated along a waveguide and blade (110) in order to tune the acoustic assembly to a preferred resonant frequency $f_o$ when the acoustic assembly is not loaded by tissue. When transducer assembly (102) is energized, the distal end of blade (110) is configured to move substantially longitudinally (along the x axis) in the range of, for example, approximately 10 to 500 microns peak-to-peak, and perhaps in the range of about 20 to about 200 microns, at a predetermined vibrational frequency $f_o$ of, for example, 55,500 Hz. The distal end of blade (110) may also vibrate in the y-axis at about 1 to about 10 percent of the motion in the x-axis. Of course, movement of blade (110) when transducer assembly (102) is energized may alternatively have any other suitable characteristics. When ultrasonic blade (110) is in an activated state (i.e., vibrating ultrasonically), ultrasonic blade (110) is operable to effectively cut through and seal tissue.

Transducer assembly (102) receives electrical power from a generator (112). In particular, transducer assembly (210) is coupled with generator (112) via an adaptor (114) and a cable (120) that is connected to a receptacle assembly (116) of generator (112). Receptacle assembly (116) provides a power and/or data input/output for connecting a surgical instrument (100) to the generator (112). Generator (112) of the present example further includes a display (118). Display (118) provides information on the generator (112) and any attached surgical instrument (100). In some versions, display (118) further provides controls or interfaces for allowing a user to change various settings of generator (112). Generator (112) further includes a power source and control module that is configured to provide a power profile to transducer assembly (102) that is particularly suited for the generation of ultrasonic vibrations through transducer assembly (102).

By way of example only, generator (112) may comprise a GEN 11 or GEN 300 sold by Ethicon Endo-Surgery, Inc. of Cincinnati, Ohio. In addition or in the alternative, generator (112) may be constructed in accordance with at least some of the teachings of U.S. Pat. No. 8,986,302, entitled "Surgical Generator for Ultrasonic and Electrosurgical Devices," issued Mar. 24, 2015, the disclosure of which is incorporated by reference herein. Still other suitable forms that generator (112) may take, as well as various features and operabilities that generator (112) may provide, will be apparent to those of ordinary skill in the art in view of the teachings herein. Adaptor (114) may also provide wider compatibility between a specific surgical instrument (100) and a specific receptacle (116) of generator (112); and may also enable additional functionality as described in further detail below.

Figure 2:
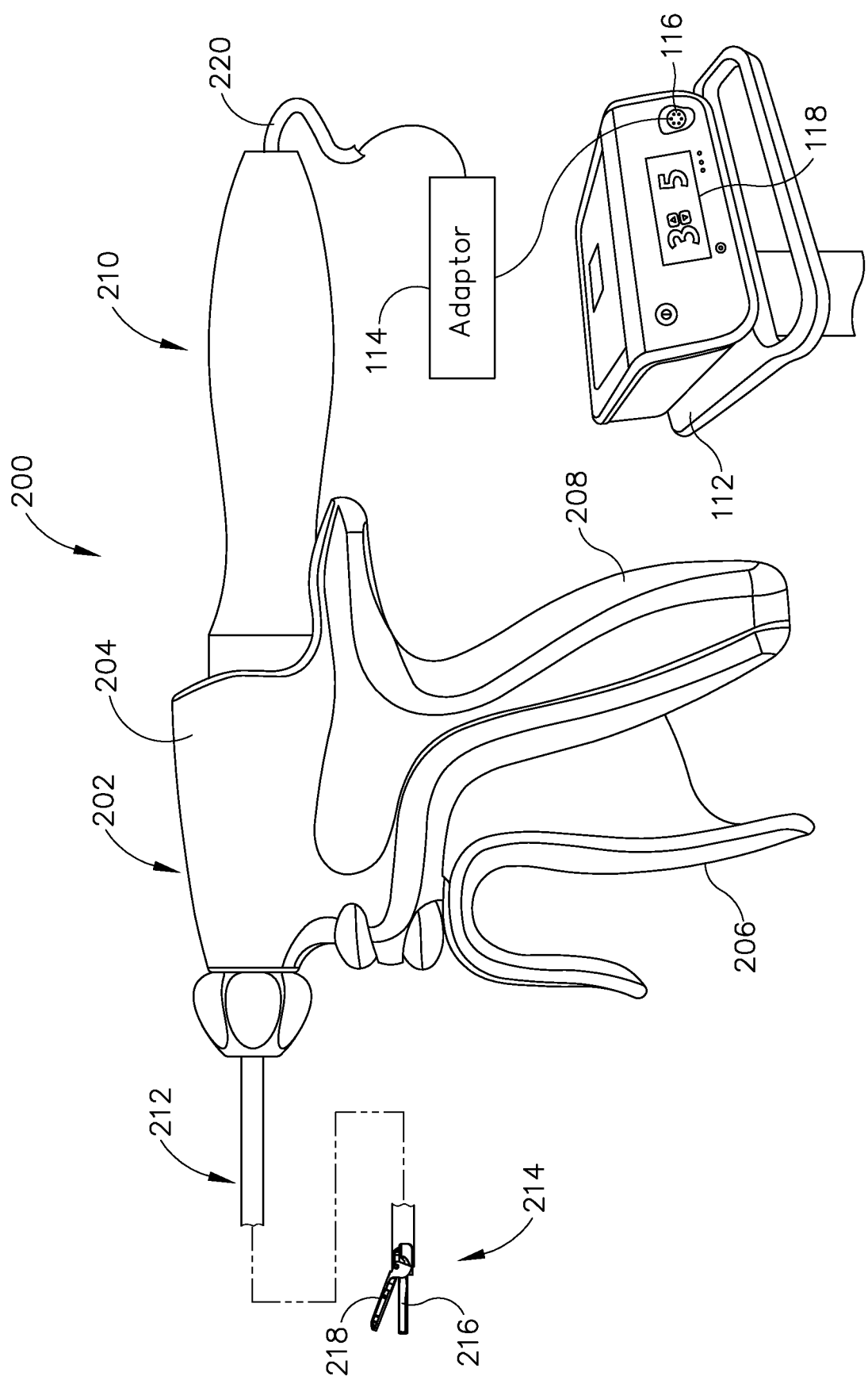
FIG. 2 depicts a side elevation view of a second exemplary surgical instrument.

FIG. 2 shows a side elevation view of another exemplary surgical instrument (200). Instrument (200) is operable to cut tissue and seal or weld tissue substantially simultaneously. It should also be understood that instrument (200) may have various structural and functional similarities with the HARMONIC ACE® Ultrasonic Shears. Furthermore, instrument (100) may have various structural and functional similarities with the devices taught in any of the other references that are cited and incorporated by reference herein.

Instrument (200) is configured to be used as a shears. Instrument (200) of this example comprises a handle assembly (202), a shaft assembly (212), and an end effector (214). Handle assembly (202) comprises a body (204) including a pistol grip (208) and a pair of buttons (126). Handle assembly (202) also includes a trigger (206) that is pivotable toward and away from pistol grip (208). It should be understood, however, that various other suitable configurations may be used, including but not limited to a pencil-grip configuration or a scissor-grip configuration. An ultrasonic transducer assembly (210) extends proximally from body (204) of handle assembly (202). Transducer assembly (210) is coupled with generator (112) via an adaptor (114) and a cable (220) connected to receptacle assembly (116). Transducer assembly (210) receives electrical power from generator (112) and converts that power into ultrasonic vibrations through piezoelectric elements. Generator (112) of the example shown in FIG. 2 is the same as the generator (112) of the example shown in FIG. 1. Other suitable forms that generator (112) may take will be apparent to those of ordinary skill in the art in view of the teachings herein.

End effector (214) includes an ultrasonic blade (216) and a pivoting clamp arm (218). Clamp arm (218) is coupled with trigger (206) such that clamp arm (218) is pivotable toward ultrasonic blade (216) in response to pivoting of trigger (206) toward pistol grip (208); and such that clamp arm (218) is pivotable away from ultrasonic blade (216) in response to pivoting of trigger (206) away from pistol grip (208). Various suitable ways in which clamp arm (218) may be coupled with trigger (206) will be apparent to those of ordinary skill in the art in view of the teachings herein.

Blade (216) of the present example is operable to vibrate at ultrasonic frequencies in order to effectively cut through and seal tissue, particularly when the tissue is being compressed between clamp arm (218) and blade (216). Blade (216) is positioned at the distal end of an acoustic drivetrain. This acoustic drivetrain includes transducer assembly (210) and an acoustic waveguide (not shown). Transducer assembly (210) includes a set of piezoelectric elements (not shown) that are located proximal to a horn (not shown) of the rigid acoustic waveguide. The piezoelectric discs are operable to convert electrical power into ultrasonic vibrations, which are then transmitted along acoustic waveguide, which extends through shaft assembly (212), to blade (216) in accordance with known configurations and techniques. By way of example only, this portion of the acoustic drivetrain may be configured in accordance with the teachings above and/or various teachings of various references that are cited herein. When ultrasonic blade (216) is in an activated state (i.e., vibrating ultrasonically), ultrasonic blade (216) is operable to effectively cut through and seal tissue, particularly when the tissue is being clamped between clamp arm (218) and ultrasonic blade (216).

Instruments (100, 200) shown in FIGS. 1-2 are merely illustrative examples of instruments that may be used with a generator (112) and an adaptor (114). By way of example only, either instrument (100, 200) may be modified and operable in accordance with the teachings of any of the various references that are cited herein. Other examples of suitable instruments will be apparent to those of ordinary skill in the art in view of the teachings herein.

II. Overview of Exemplary Adaptor

Figure 5:
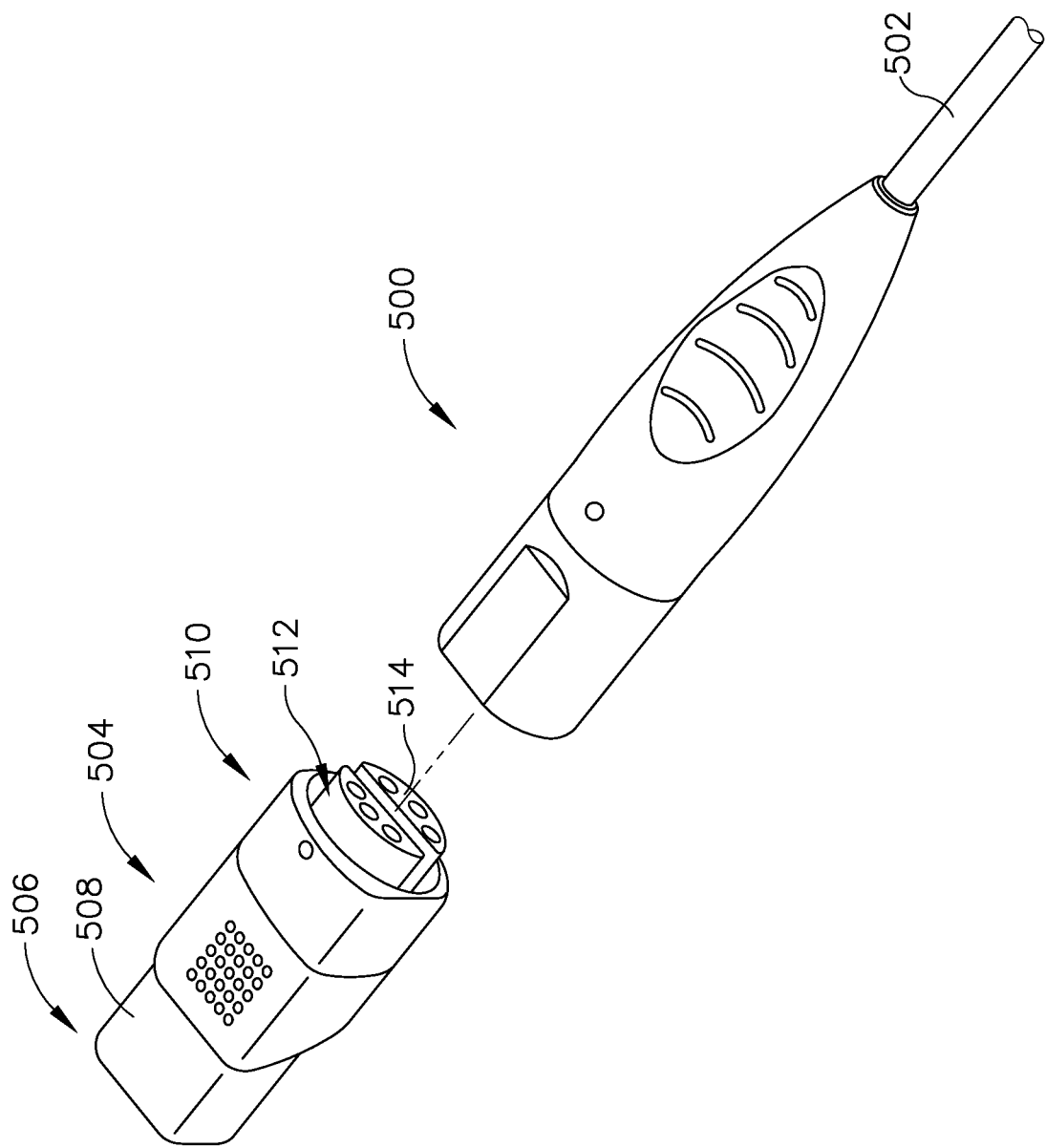
FIG. 5 depicts a perspective view of an exemplary adaptor.

FIG. 5 illustrates an adaptor assembly (504) that is configured to connect a surgical instrument (100, 200) to a generator (112). It should be understood that adaptor assembly (504) is an example of a form that the above-described adaptor (114) may take. Adaptor assembly (504) allows connector assemblies having various geometries to be electrically coupled to a receptacle assembly (116) of a surgical generator (112). In other words, adaptor assemblies (504) may be used to enable a single receptacle assembly (116) to couple with various kinds of surgical instruments having various kinds of connector assemblies. In the example shown, adaptor assembly (504) is configured to accommodate a surgical instrument (100, 200) having a connector assembly (500). Connector assembly (500) is coupled with a transducer assembly (102, 210) via a cable (502). As is to be appreciated, other versions of adaptor assemblies may accommodate surgical instruments having connector assemblies that are different from those illustrated in FIG. 5. It should also be understood that cable (502) of this example may be viewed as serving as a representation of cables (120, 220) described above.

Figure 6:
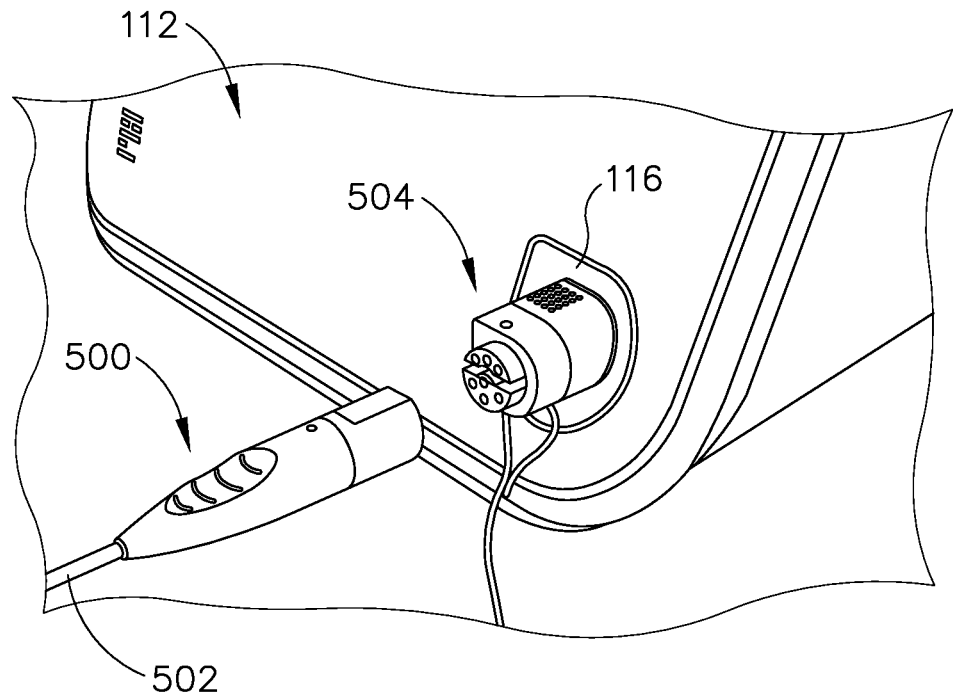
FIG. 6 depicts a perspective view of an exemplary adaptor shown in context with connecting components.
Figure 7:
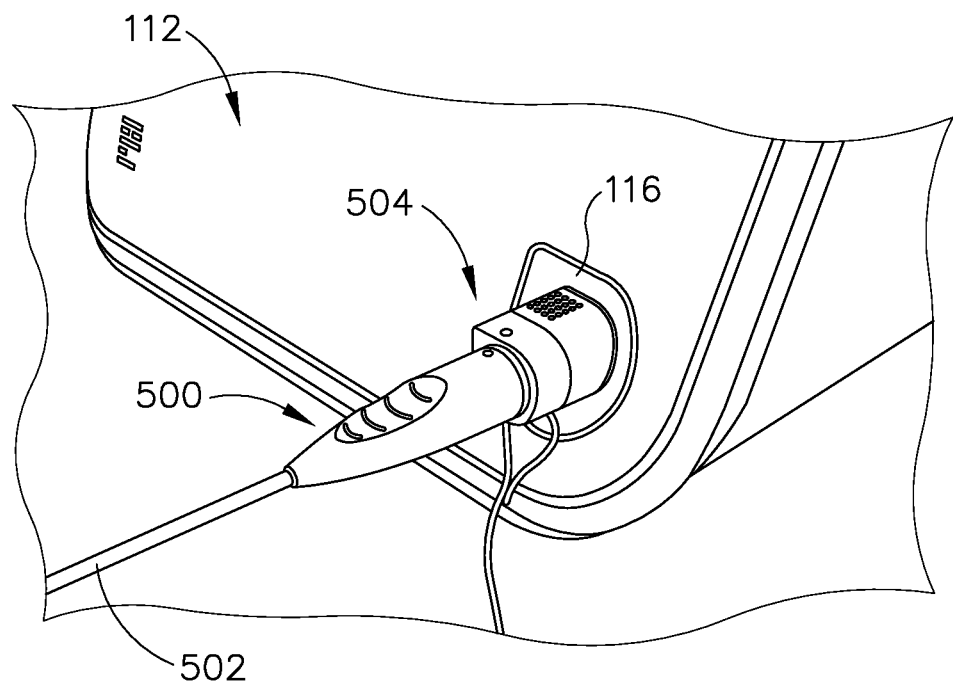
FIG. 7 depicts a perspective view of the adaptor of FIG. 6 connecting two components.

FIG. 6 illustrates adaptor assembly (504) after adaptor assembly (504) is inserted into receptacle assembly (116) of surgical generator (112) in accordance with one non-limiting example. FIG. 7 illustrates connector assembly (500) after being inserted into the adaptor assembly (504). Accordingly, a variety of connector assemblies (500), each having different geometries, may be used with surgical generator (112).

As shown in FIG. 5, adaptor assembly (504) of the present example has a distal portion (506) that comprises a projection (508). Projection (508) is configured to be inserted into receptacle assembly (116) of the surgical generator (112). Adaptor assembly (504) also has a proximal portion (510) that defines a cavity (512). In the illustrated example, a central portion (514) is positioned in the cavity (512) and is configured to accept connector assembly (500). Adaptor assembly (504) includes conductive elements that enable electrical power to be communicated from generator (112) to transducer assembly (102, 210) via receptacle assembly (116), connector assembly (500), and cable (502). In some versions, adaptor assembly (504) further includes conductive elements that enable data to be communicated between generator (112) and instrument (100, 200) via receptacle assembly (116), connector assembly (500), and cable (502). Adaptor assembly (504) may be further constructed and operable in accordance with at least some of the teachings of U.S. Pat. No. 8,986,302, entitled "Surgical Generator for Ultrasonic and Electrosurgical Devices," issued Mar. 24, 2015, the disclosure of which is incorporated by reference herein. Other suitable ways in which adaptor assembly (504) may be constructed and operable will be apparent to those of ordinary skill in the art in view of the teachings herein.

While adaptor assembly (114, 504) of the present example is shown as being interposed between connector assembly (500) and generator (112), it should be understood that variations of adaptor assembly (114, 504) may alternatively be located elsewhere. By way of example only, a variation of adaptor assembly (114, 504) may be located between cable (502) and transducer assembly (102, 210). Other suitable locations in which at least some of the components and/or functionality of adaptor assembly (114, 504) may be incorporated will be apparent to those of ordinary skill in the art in view of the teachings herein.

III. Methods for Managing Device Lifecycle In some versions, a surgical instrument (100, 200) may include an electrically erasable programmable read only memory (EEPROM) that stores certain operational data including, for example, a usage counter. In some such versions, the EEPROM may be contained within the ultrasonic transducer assembly (102, 210). Alternatively, the EEPROM may be contained in the handle assembly (104) or body (204) of instrument (100, 200); or elsewhere. The usage counter may be configured to track a total number of uses of the surgical instrument (100, 200) (e.g., the number of times transducer assembly (102, 210) was activated), the number of surgical procedures in which surgical instrument (100, 200) was used, a total duration of usage of surgical instrument (100, 200), and/or other usage related characteristics of the surgical instrument. While an EEPROM is used to provide a usage counter in the present example, it should be understood that various kinds of memory elements may be used to provide a usage counter.

When a surgical instrument (100, 200) is connected to a surgical generator (112), generator (112) may be configured to provide power to surgical instrument (100, 200) only if the usage counter of surgical instrument (100, 200) does not exceed a certain number of usages, total duration of usage, number of activations, or the like. In this manner, a manufacturer may limit the number of uses of surgical instrument (100, 200) from the factory, to prevent unlimited reuse of instrument (100, 200) and the associated risks of mechanical failure due to overuse. While there may be advantages to providing a usage based lockout at the level of instrument (100, 200), it may also create inconveniences in the case of refurbished devices, emergencies, equipment failure testing, and similar situations. Additionally, reprogramming and reconditioning of the EEPROM to allow continued use after an instrument (100, 200) expires (i.e., after usage of instrument (100, 200) has exceeded a threshold) may be inconvenient and expensive for the end user and manufacturer.

In addition to providing flexible compatibility between a variety of generators (112) and surgical instruments (100, 200), adaptor assembly (114, 504) may allow the manufacturer to provide a limited EEPROM reprogramming capability to end users. In some versions, adaptor assembly (114, 504) may include an override device within the adaptor assembly (114, 504), which may comprise a memory and/or processor that may be used to reprogram an EEPROM within surgical instrument (100, 200). When attached to a generator (112) through an adaptor assembly (114, 504), the override device will be placed in line with data and power connections between generator (112) and surgical instrument (100, 200) and may pass along data or information causing the EEPROM to be overwritten without requiring that the EEPROM be removed from surgical instrument (100, 200) and reprogrammed or reconditioned manually. Various suitable structural components and control algorithms that may be incorporated into adaptor assembly (114, 504) that may be used to provide this capability of reprogramming an EEPROM in instrument (100, 200) will be apparent to those of ordinary skill in the art in view of the teachings herein. Similarly, various suitable components and control algorithms that may be incorporated into generator (112) in order to provide such operability through adaptor assembly (114, 504) will be apparent to those of ordinary skill in the art in view of the teachings herein.

Figure 8:
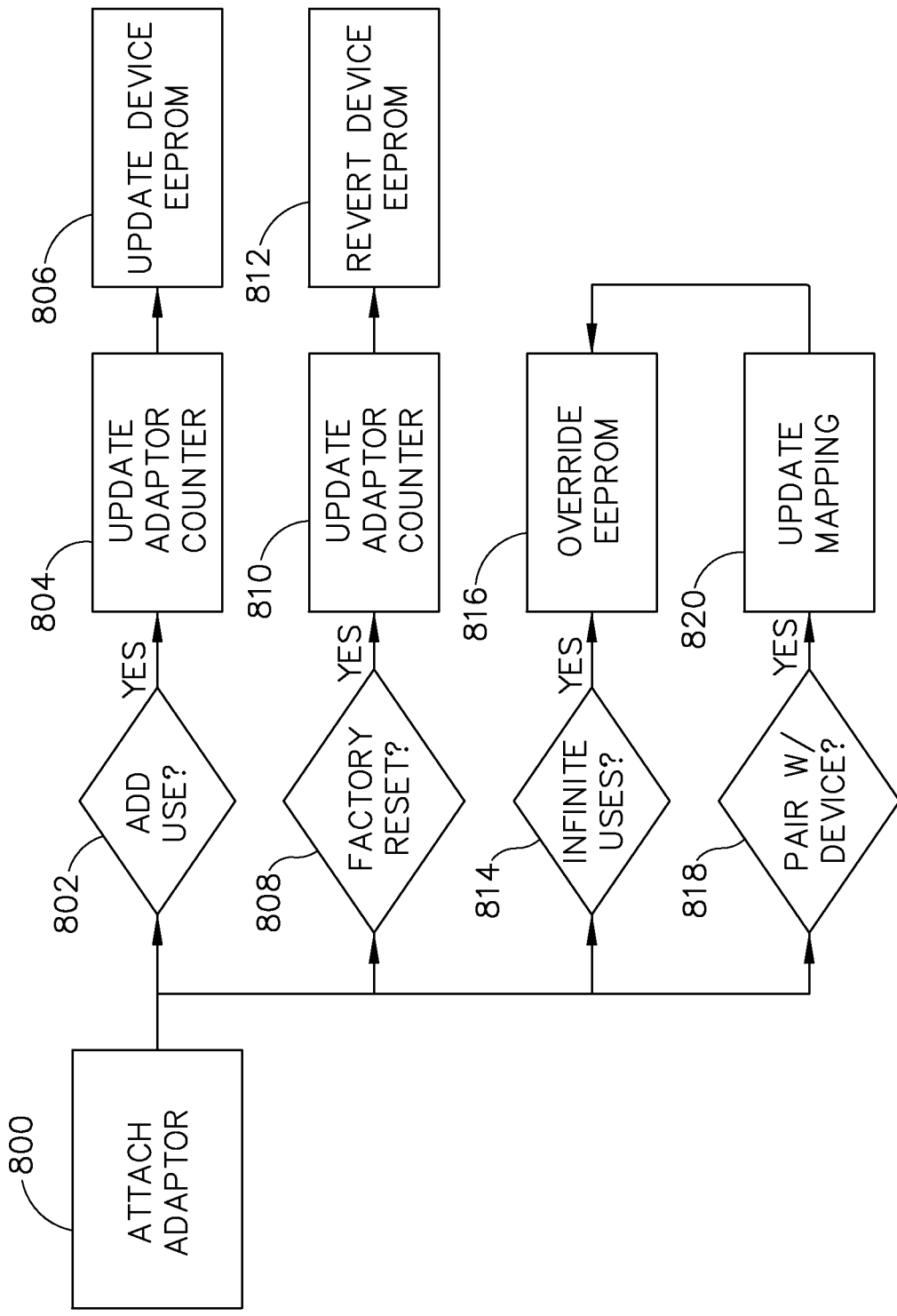
FIG. 8 depicts a flowchart of an exemplary set of steps that a system could perform to modify the operation of a connected surgical instrument.

FIG. 8 shows a flowchart of an exemplary set of steps that a system could perform to modify the operation of a connected surgical instrument (100, 200) via adaptor assembly (114, 504). When a surgical instrument (100, 200) is attached (block 800) to a generator (112) by way of adaptor assembly (114, 504), one or more actions may occur depending upon the configuration of the override device within adaptor assembly (114, 504). If the override device is configured to add additional device uses to an EEPROM (block 802), when a connection between adaptor assembly (114, 504) and connector assembly (500) is established (block 800), the override device may update an internal override counter (block 804). The override counter may be used to prevent the override device from being used an unlimited number of times. So, for example, when an override counter reaches a certain number it will be prevented from adding uses (block 802) to further surgical instruments (100, 200). Additionally, the EEPROM of surgical instrument (100, 200) will receive a set of signals from the override device causing the usage counter to be updated (block 806) and, in effect, reduce the detectable usage of instrument (100, 200) as perceived by generator (112).

As an example, suppose an instrument (100) was purchased in an unused state and contained an EEPROM with a usage counter initially showing zero uses. Instrument (100) is then used ten times during various procedures, and the usage counter now shows ten uses. When connected to an adaptor assembly (114, 504) that is configured to add additional uses to instrument (100), the usage counter may reduced back to zero (block 806); or may be reduced by a set amount such as five uses, or any other number of desirable uses. Adaptor assembly (114, 504) itself in this example has an override counter of one. If a generator (112) is configured to place instrument (100) into a lockout mode after ten uses, instrument (100) will not function when the usage counter indicates ten uses have occurred. However, after the usage counter is decremented (804) by adaptor assembly (114, 504), generator (112) will detect that instrument (100) has been used less than ten times, and will allow a number of additional usages until the usage counter reaches ten again. When used to modify the EEPROM (block 806), adaptor assembly (114, 504) override counter will be reduced to zero (804), so that if adaptor assembly (114, 504) is attached to a further surgical instrument (100, 200), adaptor assembly (114, 504) will be unable to add uses (block 802).

In some versions, the override device may be further configured to maintain an internal mapping of surgical instruments (100, 200) that have been modified so that a particular surgical instrument (100, 200) may only have its EEPROM updated (block 806) a single time. So, for example, if a particular adaptor assembly (114, 504) is configured to allow five surgical instruments (100, 200) to have their EEPROM be updated (block 806) to allow additional uses, adaptor assembly (114, 504) may maintain an internal listing of the serial numbers of each surgical instrument (100, 200) that adaptor assembly (114, 504) is used with by pulling the unique identifier from the EEPROM as the EEPROM is updated. In this manner, the manufacturer of adaptor assembly (114, 504) can ensure that adaptor assembly (114, 504) is used to enable usage of five different surgical instruments (100, 200), rather than being used to enable a single surgical instrument (100, 200) to be used five times and thereby potentially enabling dangerous overuse.

The lifecycle of new and reconditioned devices may be managed as described above, or may, in addition or in the alternative, be managed in different ways. Some adaptor assemblies (114, 504) may be configured to perform a factory reset (block 808) of a surgical instrument (100, 200)

that is attached (block 800) to adaptor assembly (115, 504). This would function similarly to adding uses (block 802) but would revert the EEPROM of the attached instrument (100, 200) to its factory state (block 812) and, in doing so, would reduce the instrument (100, 200) usage counter to its factory state. The override device may be configured to maintain an override counter and update the override counter (block 810) upon each factory reset to prevent unlimited reversions. The override device may also be configured to maintain an internal mapping of uniquely identified surgical instruments (100, 200) that have been reverted in this manner, to prevent unlimited reversions of the same instrument (100, 200), which could result in dangerous overuse.

An additional use of the override device would be to allow infinite usage (block 814) of surgical instrument (100, 200), completely overriding its EEPROM usage counter (block 816). This approach could be useful in testing scenarios where a manufacturer or certifying agency might want to test the boundaries of the performance of instrument (100, 200) without being restrained by usage counter lockout. Yet another use of the override device would be to manage all additional usages with the override device itself rather than overwriting EEPROMs of surgical instruments (100, 200). This could be accomplished by configuring the override device of adaptor assembly (114, 504) to pair with a limited number of surgical instruments (100, 200) upon attachment (block 800) and maintain a list of each paired surgical instrument (100, 200) and the number of additional uses that have been allowed (block 820). In this manner, the paired surgical instrument (100, 200) EEPROM is not changed, but adaptor assembly (114, 504) itself is able to identify each surgical instrument (100, 200) that adaptor assembly (114, 504) has been paired with; and the number of additional uses that each paired instrument (100, 200) has been allowed.

Since the override device itself is managing the mapping (block 820), the EEPROM of the paired surgical instrument (100, 200) would be overridden (816) and allowed to function so long as the managed mapping (820) allows for additional usages of the paired surgical instrument (100, 200). This could be advantageous where certain EEPROM have limited rewrite capability or are prone to data corruption upon rewrite, for example. Additionally, this feature could be used to enable a limited compatibility between a generator (112) from a first manufacturer and a surgical instrument (100, 200) from a second manufacturer where, for example, the second manufacturer does not track device usage in the manner that generator (112) is expecting. For example, a surgical instrument (100, 200) from a second manufacturer may not store within an EEPROM the usage characteristics that a generator (112) from a first manufacturer will verify before allowing surgical instrument (100, 200) to operate. An adaptor assembly (114, 504) storing a device mapping (820) could allow a limited number of non-compliant surgical instruments (100, 200) to function despite not having the expected EEPROM usage contents.

In some versions, EEPROM may be written with additional data upon an EEPROM update (block 806) or reversion (block 812). For example, a rewrite flag may be set within the EEPROM upon an update (block 806) or reversion (block 812) indicating that the EEPROM has been rewritten one or more times since its factory state. This rewrite flag may be detected in future instances where an adaptor assembly (114, 504) is attached (block 800) and attempts to add uses (block 802) or perform a factory reset (block 808) and prevent the operation from completing. This could be used to prevent unlimited reuse of particular instruments (100, 200), and could be used in additionally or alternatively with a record of rewritten instruments (100, 200) maintained internally by the override device.

In some versions, adaptor assembly (114, 504) and integrated override device may be configured to communicate with an external system to assist in managing data. For example, adaptor assembly (114, 504) may contain a wireless communication capability such as WiFi, may be integrated with a wired communication capability such as Micro USB, or may be paired with a docking device that itself integrates such communication capability. As another merely illustrative example, such communication capability may be incorporated into generator (112). As the override device is used to connect with surgical instruments (100, 200), update (block 806) or revert EEPROM (block 812) or pair with devices (block 818) and maintain usage mapping (block 820), it will create and store potentially useful data describing a variety of real world usages of adaptor assembly (114, 504) and connected surgical instruments (100, 200).

For example, an adaptor assembly (114, 504) communicating with an external server could provide data identifying the particular serial numbers of surgical instruments (100, 200) that adaptor assembly (114, 504) has been attached with, surgical instruments (100, 200) that have had an EEPROM updated or modified, times and dates of such occurrences, locations of such occurrences, and the like. Such information could be useful in tracking a certain surgical instrument (100, 200) and determining if it has been used in a manner not recommended by the manufacturer (e.g., by updating the EEPROM multiple times), could track missing or stolen surgical instruments (100, 200), could detect when a particular user may need to purchase additional surgical instruments (100, 200) or adaptor assemblies (114, 504), and other similar information. This could additionally provide opportunities to "recharge" an adaptor assembly (114, 504) remotely, where, for example, an adaptor assembly (114, 504) override counter has been reduced to zero. In such a scenario, an adaptor assembly (114, 504) could be connected to an external system and, based upon a transaction or other occurrence, have its override counter reduced or incremented to allow additional overrides.

It should be understood that when use or uses of a surgical instrument is discussed, such as adding uses (block 802) and allowing infinite uses (block 814), this could include both full usage of a surgical instrument (100, 200), as well as selective enablement of certain features of a surgical instrument (100, 200). For example, some versions of surgical instrument (100, 200) may provide a basic functionality and an advanced functionality. For instance, a basic functionality or mode of operation may provide a sustained delivery of ultrasonic energy, at a consistent power level, to tissue in response to actuation of buttons and/or other user input features of instrument (100, 200). An advanced functionality or mode of operation may provide adaptive delivery of ultrasonic energy at a power level that varies in real time based on sensed tissue conditions (e.g., tissue temperature, tissue impedance, etc.). Where such varying functionalities or modes of operation are available, adaptor (114) may be configured to modify the usage counter such that only the basic functionality is restored for a certain number of uses; or may be configured to modify the usage counter to restore basic functionality and at least some aspects of the advanced functionality for a certain number of total or individual uses between the two feature sets, while still preventing use of at least some other aspects of the adaptive functionality. This may be useful where, for example, reconditioning and reuse of devices may be determined to be safe for the basic functionality of the device, while advanced or adaptive features may only be verifiably safe with brand new surgical instruments (100, 200). This may also be useful where, for example, a surgical instrument (100, 200) was not originally configured to allow a certain functionality, such as the adaptive cutting functionality, and it is later determined that the surgical instrument (100, 200) is able to safely perform the adaptive cutting functionality but is unable to do so because the generator (112) determines that the surgical instrument (100, 200) lacks the configuration to support the functionality. In this scenario, the adaptor (114) may modify the surgical instrument (100, 200) EEPROM to support the functionality in question, or may override communications between the surgical instrument (100, 200) and the generator (112) so that the functionality may be supported. Other examples of features of a surgical instrument (100, 200) being partially or fully enabled will be apparent in light of the disclosure herein.

Figure 9:
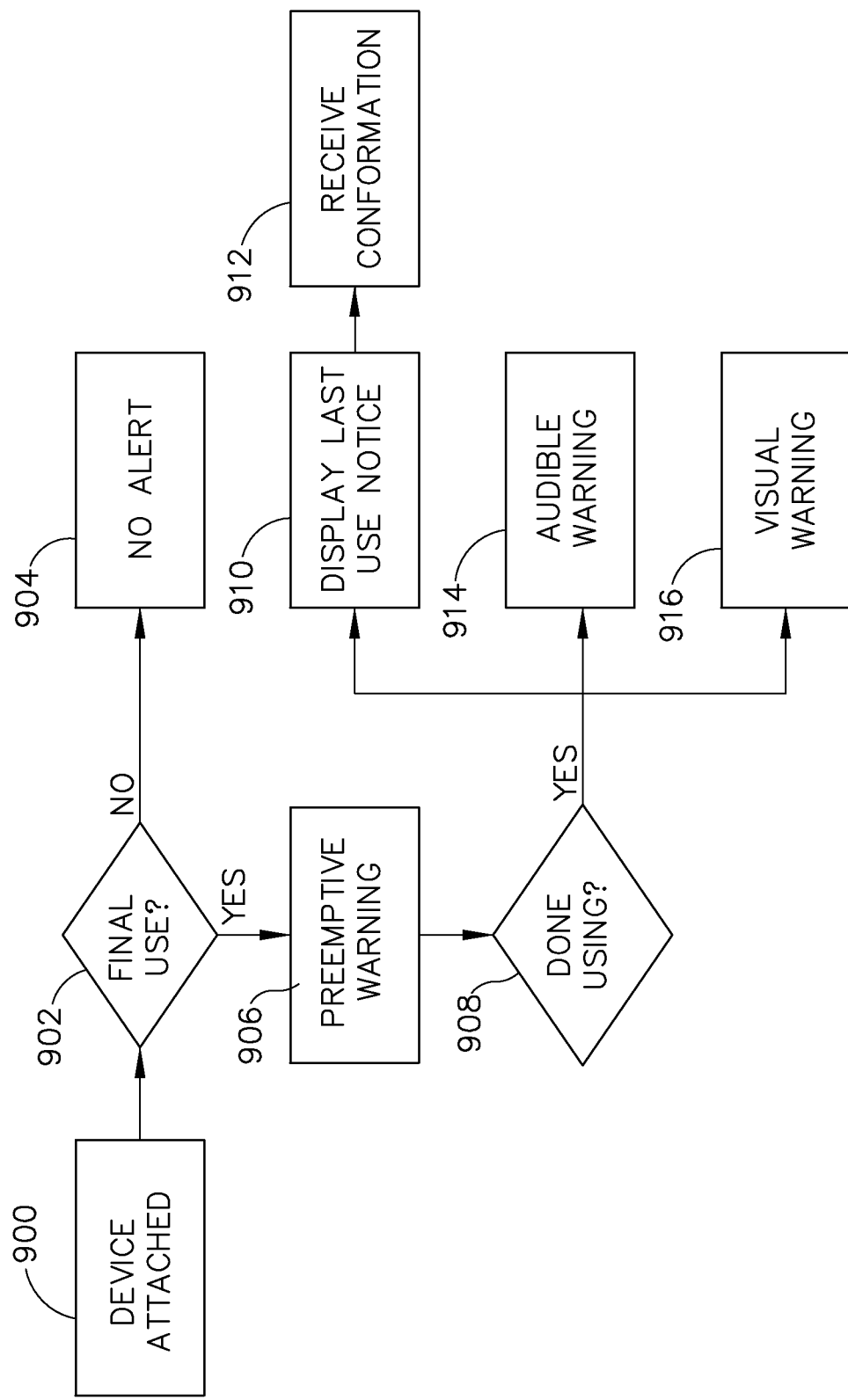
FIG. 9 depicts a flowchart of an exemplary set of steps that a system could perform to notify a user of a depleted surgical instrument.

FIG. 9 shows a flowchart of an exemplary set of steps that a system could perform to notify a user of a depleted surgical instrument (100, 200). The steps in FIG. 9 may be performed in conjunction with or independently of the adaptor assembly (114, 504) discussed above. When a surgical instrument (100, 200) is attached (block 900), generator (112) may access surgical instrument (100, 200) EEPROM and determine, based upon a usage counter, whether surgical instrument (100, 200) is at or near its final use before a usage based lockout mode is enabled (902). If the attached instrument (100, 200) is not at or near a final use (block 902), then no alert occurs (block 904) and operation is normal. If the attached instrument (100, 200) is at a final use (block 902), generator (112) may provide a preemptive warning via display (118) or another device of generator (112). The preemptive warning may be a visual or audible indicator, and may in some cases provide a textual or audible explanation.

When the use of instrument (100, 200) is complete (block 908), as indicated by the powering down or disconnection of instrument (100, 200), instrument (100, 200) and/or generator (112) may perform one or more additional actions to notify a user that the final use of instrument (100, 200) has occurred. These actions could include, for example, displaying via generator (112) or a display of instrument (100, 200) a notification indicating that the final use has occurred and instrument (100, 200) has expired (block 910). Such a notification may also display a button or prompt on a touch screen display (e.g., on display (118)) requiring that the user touch the button or otherwise acknowledge the notification (block 912). Another action could include causing an audible notification to emit from generator (112), surgical instrument (100, 200), or both. The audible warning could be an intermittent beep or tone, or could be an automated voice message explaining that surgical instrument (100, 200) is expired. Such a beep, tone, or voice could continue until an additional button of generator (112) or surgical instrument (100, 200) is actuated to indicate that the warning has been acknowledged. Another action could include a visual warning (block 916) such as an LED or other visual indicator of generator (112) or surgical instrument (100, 200) lighting, flashing, or otherwise visually indicating that instrument (100, 200) has expired. The visual warning (block 916) could continue until the user presses a button to acknowledge the warning.

The preemptive and subsequent warnings relating to surgical instrument (100, 200) usage and expiration may be useful to users of surgical instrument (100, 200) because it allows the user to account for the impending expiration of surgical instrument (100, 200) rather than discovering that a surgical instrument (100, 200) has already expired when it is presently needed. For example, without the described warning, a surgical instrument (100, 200) may be used for a surgical procedure and its usage counter may be incremented, resulting in the surgical instrument (100, 200) expiring at the end of the surgical procedure; but no expiration notice is provided when surgical instrument (100, 200) is powered down or disconnected from the generator (112). Rather than being disposed of or placed in a storage area for expired devices, the expired surgical instrument (100, 200) might be taken to be sanitized and prepared for a subsequent surgical procedure. During a subsequent surgical procedure, surgical instrument (100, 200) is connected to the generator (112), and only then does the user discover that surgical instrument (100, 200) has expired, requiring a delay in the procedure while a usable surgical instrument (100, 200) is located and prepared.

Configuring a generator (112) and/or surgical instrument (100, 200) to perform the steps of FIG. 9 resolves the inefficient and potentially dangerous inability to appropriately react to expiration of an instrument (100, 200). Supposing the same surgical instrument (100, 200) described above being used in a procedure for its final use before a usage counter causes it to enter lockout mode, when surgical instrument (100, 200) is attached to generator (112) it is determined that surgical instrument (100, 200) is on its final use (902). A notification may be displayed via the display (118) of the generator (112) indicating that surgical instrument (100, 200) has only one use remaining, and will thus be expired after the present surgical procedure. After the surgical procedure, when surgical instrument (100, 200) is powered down or disconnected from generator (112), generator (112) displays an additional message or notification via display (118) explaining that surgical instrument (100, 200) is now expired and should be treated appropriately. Generator (112) may continue to display this notification and prevent further use until an acknowledgment is received (912) from the user that the expired surgical instrument (100, 200) has been handled appropriately. Additionally, an audible tone (914) or flashing LED (918) indicator may be activated on the surgical instrument (100, 200) and continue after the device is powered down or disconnected from generator (112). The audible tone or flashing LED may continue until manually acknowledged or until a power supply, such as a battery or capacitor, within the surgical instrument (100, 200) is drained. In this manner, users of a soon to be expired surgical instrument (100, 200) are given several opportunities, some requiring action, to acknowledge that surgical instrument (100, 200) has expired and avoid wasteful post procedure activities with surgical instrument (100, 200), as well as avoid potentially dangerous reliance on an expired surgical instrument (100, 200) during subsequent procedures.

Figure 3:
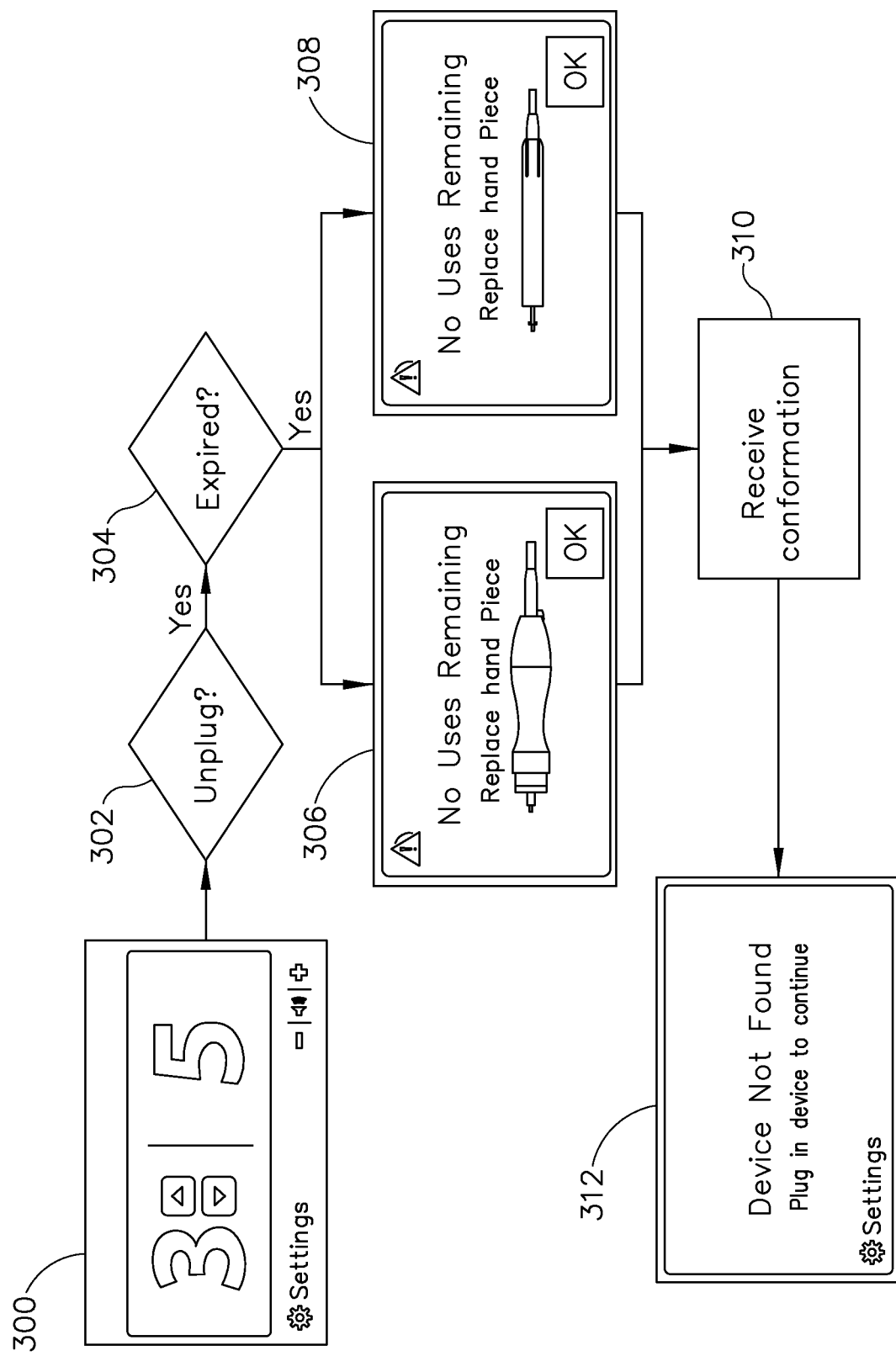
FIG. 3 depicts a flowchart showing exemplary interfaces displayed by a generator in response to events.
Figure 4:
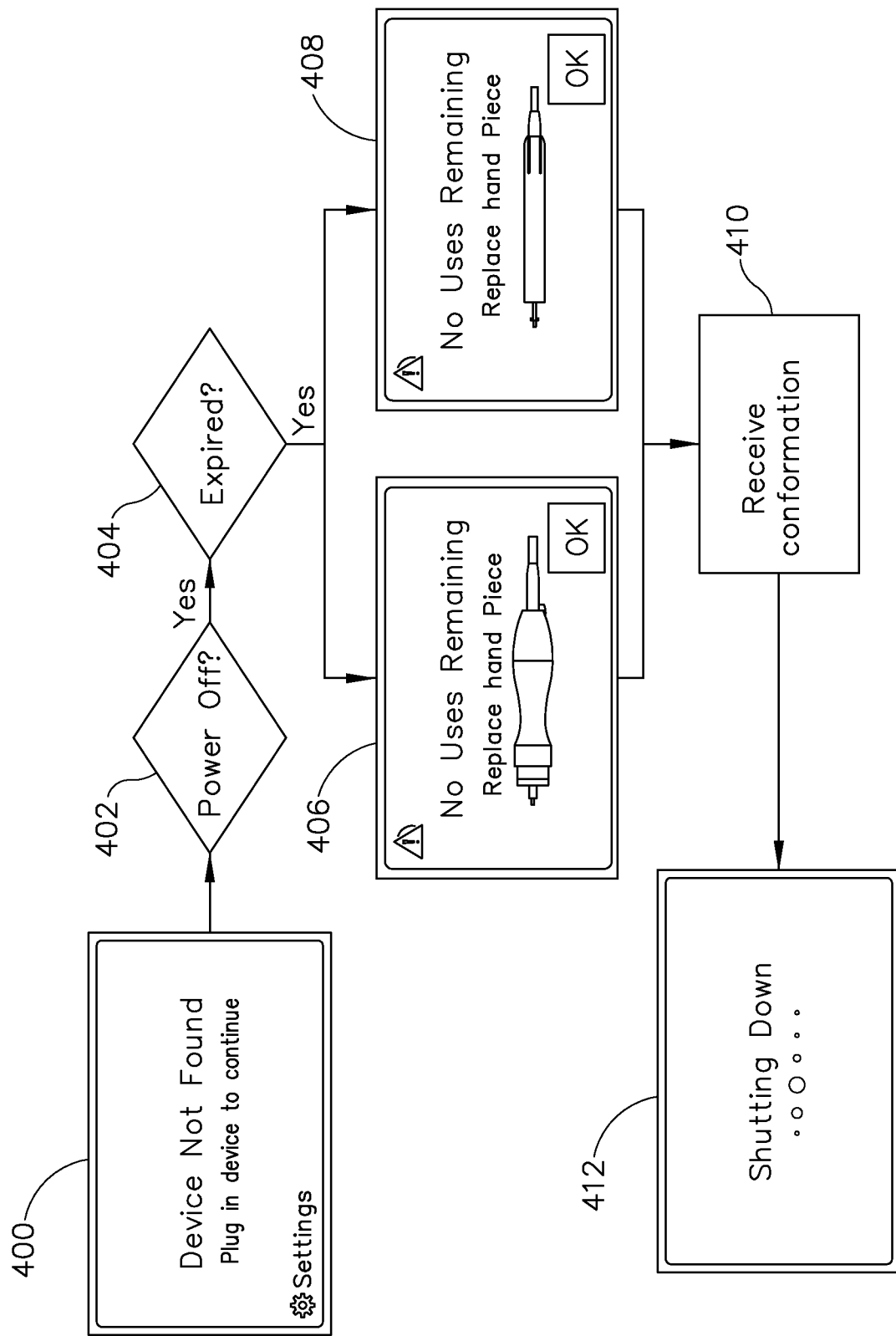
FIG. 4 depicts a flowchart showing additional exemplary interfaces displayed by a generator in response to events.

FIGS. 3 and 4 show exemplary interfaces and steps that could be performed to provide the notification functionality described above in the context of FIG. 9. Referring to FIG. 3, display (118) of generator (112) may initially show an operation interface (300) with information and controls for normal operation of generator (112) and surgical instrument (100, 200) while surgical instrument (100, 200) is attached to generator (112). When surgical instrument (100, 200) is unplugged (block 302) from generator (112), generator (112) will examine data from the EEPROM usage counter of surgical instrument (100, 200) and determine if it is now expired (block 304). If the generator (112) determines that the recently removed surgical instrument (100, 200) is expired (block 304), generator (112) will generate an interface notification via display (118) appropriate for surgical instrument (100, 200) that has expired.

For example, in the case of instrument (200), transducer assembly (210) is configured to be re-used a certain number of times; while the rest of instrument (200) is configured to only be used once (or some other number of times). Display (118) shows a notification (306) indicating that instrument (200) has expired and advising the operator to dispose of or replace transducer assembly (210). This notification (306) includes a graphical representation of transducer assembly (210). In some versions, different portions of instrument (200) are capable of being reused a different number of times. In such versions, display (118) may provide a notification (306) with a graphical representation of the particular component that has reached its maximum number of uses. Display (118) may also provide text to accompany the graphical representation, with the text advising the user that the expired component has reached its maximum number of uses; and instructing the user to replace the expired component.

Similarly, in the case of instrument (100), transducer assembly (102) is configured to be re-used a certain number of times; while the rest of instrument (100) is configured to only be used once (or some other number of times). Display (118) shows a notification (308) indicating that instrument (100) has expired and advising the operator to dispose of or replace transducer assembly (102). This notification (308) includes a graphical representation of transducer assembly (102). In some versions, different portions of instrument (100) are capable of being reused a different number of times. In such versions, display (118) may provide a notification (308) with a graphical representation of the particular component that has reached its maximum number of uses. Display (118) may also provide text to accompany the graphical representation, with the text advising the user that the expired component has reached its maximum number of uses; and instructing the user to replace the expired component.

Notification (306, 308) may also have a prompt such as an "OK" or "NEXT" button that requires a user to interact with display (118) or generator (112) before a subsequent use in order to confirm (310) that the user has received the expired device notification (306, 308). Once confirmation is received (block 310), generator (112) may display a non-operation interface (312) indicating that generator (112) is ready for a subsequent use with a different surgical instrument (100, 200). Operating in the manner described in the context of FIG. 3, when a surgical instrument (100, 200) expires after use with a generator (112), generator (112) will require a user acknowledgment that surgical instrument (100, 200) is now expired before returning to an operational state.

Referring to FIG. 4, display (118) of generator (112) may initially show a non-operation interface (400) immediately before shut down of generator (112). When generator (112) is powered off (block 402), generator (112) will determine if any surgical instrument (100, 200) was recently used that is now expired (404). This may be done by examining the generator's (112) records of instruments (100, 200) attached since generator (112) was last powered on; and whether the EEPROM of any of those instruments (100, 200) indicate that the instrument (100, 200) only had one usage remaining. If any instruments (100, 200) were used that are now expired (block 404), generator (112) may display an appropriate notification describing instrument (100, 200) or component that is now expired. For example, if instrument (200) was used and is now expired, display (118) may show a notification (406) similar to notification (306) described above. If instrument (100) was used and is now expired, the display (118) may show a notification (408) similar to notification (308) described above.

The notification interfaces (406, 408) may also include a button or prompt to interact with display (118) to acknowledge the notification; and generator (112) may delay shutting down until a confirmation is received (block 410) from the user. Once the confirmation is received (block 410), generator (112) may display a shut down interface (412). Operating in the manner described above in the context of FIG. 4, when a surgical instrument (100, 200) expires after use with a generator (112), generator (112) will require a user acknowledgment that instrument (100, 200) is now expired before shutting down.

IV. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus comprising: (a) a surgical generator comprising an instrument receptacle; and (b) an adaptor, the adaptor comprising a first end, a second end, and an override chip, wherein the first end of the adaptor is shaped to fit the instrument receptacle, wherein the second end of the adapter is shaped to fit a surgical instrument connector; wherein the surgical generator is configured to, upon being connected to a surgical instrument via the adaptor, receive a set of usage data from a memory of the surgical instrument; wherein the surgical generator is further configured to prevent operation of the surgical instrument based upon the set of usage data; wherein the override chip is configured to modify the set of usage data before it is received by the surgical generator.

Example 2

The apparatus of Example 1, wherein the override chip is configured to modify the set of usage data by modifying the contents of the memory of the surgical instrument.

Example 3

The apparatus of any one or more of Examples 1 through 2, wherein the override chip is configured to modify the set of usage data by creating an override set of usage data, and wherein the override chip is configured to replace the set of usage data with the override set of usage data before the set it is received by the surgical generator.

Example 4

The apparatus of any one or more of Examples 1 through 3, wherein the set of usage data from the memory comprises a usage counter, wherein the usage counter indicates an amount of usage of the surgical instrument since its manufacture.

Example 5

The apparatus of Example 4, wherein the override chip is configured to modify the set of usage data by reducing the amount of usage of the surgical instrument.

Example 6

The apparatus of any one or more of Examples 1 through 5, wherein the override chip stores a set of override data, wherein the override chip is configured to modify the set of override data in response to the set of usage data being modified.

Example 7

The apparatus of Example 6, wherein the set of override data comprises: (i) an override counter indicating the number of times the override chip has been used to modify the set of usage data, and (ii) an override map uniquely identifying one or more surgical instruments whose usage data has been modified by the override chip.

Example 8

The apparatus of Example 7, wherein the override chip is configured to only modify the set of usage data when the override counter does not exceed a configured limit.

Example 9

The apparatus of any one or more of Examples 1 through 8, wherein the override set of usage data is configured to prevent the surgical generator from preventing operation of the surgical instrument.

Example 10

The apparatus of any one or more of Examples 1 through 9, wherein the override chip is configured to modify the set of usage data by adding an override flag, wherein the override flag indicates that the memory has been previously modified, and wherein the override chip is further configured to only modify the memory when the override flag is not present.

Example 11

The apparatus of any one or more of Examples 1 through 10, wherein the surgical generator is manufactured by a first manufacturer, wherein the surgical instrument is manufactured by a second manufacturer, and wherein the surgical instrument is only operable with the surgical generator after the set of usage data has been modified.

Example 12

The apparatus of any one or more of Examples 1 through 11, further comprising an external server, wherein the adaptor comprises a communication port in communication with the external server, wherein the adaptor is configured to send a set of override data to the external server.

Example 13

The apparatus of any one or more of Examples 1 through 12, wherein the set of usage data comprises a plurality of sets of feature data, wherein a set of feature data of the plurality of sets of feature data indicates the number of times a particular feature of the surgical instrument has been used, wherein the override chip is configured to modify the set of usage data before it is received by the surgical generator by modifying the set of feature data to allow for additional use of the particular feature.

Example 14

An apparatus comprising: (a) a surgical generator comprising an instrument receptacle and a display; and (b) a surgical instrument comprising a generator connection, the generator connection adapted to be connected to the instrument receptacle; wherein the surgical generator is configured to, upon being connected to a surgical instrument, receive a set of usage data from a memory of the surgical instrument; wherein the surgical generator is configured to determine if the set of usage data indicates that the surgical instrument will become inoperable after being used for a present procedure; wherein the surgical generator is configured to receive a signal indicating that the surgical instrument is no longer in use; wherein the surgical generator is configured to, in response to a determination that the surgical instrument will become inoperable and the signal indicating that the surgical instrument is no longer in use, provide a notification that the device is inoperable for subsequent uses.

Example 15

The apparatus of Example 14, wherein the notification that the device is inoperable for subsequent uses comprises one or more of: (i) a text notification via the display, (ii) a light emitting from a light indicator of the surgical instrument, and (iii) a tone emitting from a speaker of the surgical instrument.

Example 16

The apparatus of any one or more of Examples 14 through 15, wherein the notification that the device is inoperable for subsequent uses comprises an acknowledgment prompt, and wherein the surgical generator is configured to prevent normal operation until a signal is received indicating that a user has acknowledged the acknowledgment prompt.

Example 17

The apparatus of Example 16, wherein the signal indicating that the surgical instrument is no longer in use is caused by the disconnection of the surgical generator connection from the instrument receptacle.

Example 18

The apparatus of any one or more of Examples 16 through 17, wherein the signal indicating that the surgical instrument is no longer in use is caused by a user interaction with the surgical generator causing the surgical generator to be powered off.

Example 19

An apparatus comprising: (a) a surgical generator comprising an instrument receptacle and a display; (b) a surgical instrument comprising a generator connection; and (c) an adaptor, the adaptor comprising a first end, a second end, and an override chip, wherein the first end of the adaptor is shaped to fit the instrument receptacle, wherein the second end of the adapter is shaped to fit the generator connection, wherein the surgical generator is configured to connect to the surgical instrument via the adaptor; wherein the surgical generator is further configured to, upon being connected to the surgical instrument, receive a set of usage data from a memory of the surgical instrument; wherein the surgical generator is further configured to determine if the set of usage data indicates that the surgical instrument will become inoperable after being used for a present procedure; wherein the surgical generator is further configured to receive a signal indicating that the surgical instrument is no longer in use; wherein the surgical generator is further configured to, in response to a determination that the surgical instrument will become inoperable and the signal indicating that the surgical instrument is no longer in use, provide a notification that the device is inoperable for subsequent uses; wherein the adaptor is operable to modify the set of usage data on the memory and reduce a usage indicator of the set of usage data; and wherein the surgical instrument is configured to become operable in response to the usage indicator being reduced by the adaptor.

Example 20

The apparatus of Example 19, further comprising a plurality of reconditioned surgical instruments, each of the plurality of reconditioned surgical instruments storing an instrument identifier and a reconditioned device usage data, wherein the adaptor is configured to store a set of instrument identifiers, and wherein the adaptor is configured to modify a reconditioned device usage data only when the instrument identifier is present in the set of instrument identifiers.

V. Miscellaneous

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Other types of instruments into which the teachings herein may be incorporated will be apparent to those of ordinary skill in the art.

It should also be understood that any ranges of values referred to herein should be read to include the upper and lower boundaries of such ranges. For instance, a range expressed as ranging "between approximately 1.0 inches and approximately 1.5 inches" should be read to include approximately 1.0 inches and approximately 1.5 inches, in addition to including the values between those upper and lower boundaries.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus, comprising:
   (a) a surgical generator comprising an instrument receptacle and a display; and
   (b) a surgical instrument comprising a generator connection and an instrument indicator, the generator connection adapted to be connected to the instrument receptacle,
   wherein the surgical generator is configured to, upon being connected to the surgical instrument, receive a set of usage data from a memory of the surgical instrument,
   wherein the surgical generator is configured to determine if the set of usage data indicates that the surgical instrument will become inoperable after being used for a present procedure,
   wherein the surgical generator is configured to receive a signal indicating that the surgical instrument is no longer in use,
   wherein the surgical generator is configured to, in response to a determination that the surgical instrument will become inoperable and the signal indicating that the surgical instrument is no longer in use, provide a notification that the surgical instrument is inoperable for subsequent uses, and
   wherein the instrument indicator is configured to activate in response to the determination that the surgical instrument will become inoperable and the signal indicating that the surgical instrument is no longer in use.

2. The apparatus of claim 1, wherein the notification that the surgical instrument is inoperable for subsequent uses comprises one or more of:
   (i) a text notification via the display,
   (ii) a light emitting from a light indicator of the surgical instrument, and
   (iii) a tone emitting from a speaker of the surgical instrument.

3. The apparatus of claim 1, wherein the notification that the surgical instrument is inoperable for subsequent uses comprises an acknowledgment prompt, and wherein the surgical generator is configured to prevent normal operation until a signal is received indicating that a user has acknowledged the acknowledgment prompt.

4. The apparatus of claim 3, wherein the signal indicating that the surgical instrument is no longer in use is caused by disconnecting the generator connection from the instrument receptacle.

5. The apparatus of claim 3, wherein the signal indicating that the surgical instrument is no longer in use is caused by a user interaction with the surgical generator causing the surgical generator to be powered off.

6. The apparatus of claim 1, wherein the surgical instrument further comprises an internal power source and the instrument indicator includes a light indicator, wherein the light indicator is configured to, once activated, be permanently activated and emit light until the internal power source is expended.

7. The apparatus of claim 1, wherein the surgical instrument further comprises an internal power source and the instrument indicator includes a sound indicator, wherein the sound indicator is configured to, once activated, be permanently activated and emit audible tones until the internal power source is expended.

8. An apparatus, comprising:
   (a) a surgical generator comprising an instrument receptacle and a display;
   (b) a surgical instrument comprising a generator connection and a memory; and
   (c) an adaptor, the adaptor comprising a first end, a second end, and an override chip, wherein the first end of the adaptor is shaped to fit the instrument receptacle, wherein the second end of the adapter is shaped to fit the generator connection, wherein the surgical generator is configured to connect to the surgical instrument via the adaptor,
   wherein the surgical generator is further configured to, upon being connected to the surgical instrument, receive a set of usage data from the memory of the surgical instrument,
   wherein the surgical generator is further configured to determine if the set of usage data indicates that the surgical instrument will become inoperable after being used for a present procedure,
   wherein the surgical generator is further configured to receive a signal indicating that the surgical instrument is no longer in use,
   wherein the surgical generator is further configured to, in response to a determination that the surgical instrument will become inoperable and the signal indicating that the surgical instrument is no longer in use, provide a notification that the surgical instrument is inoperable for subsequent uses,
   wherein the adaptor is configured to modify the set of usage data on the memory and reduce a usage indicator of the set of usage data, and
   wherein the surgical instrument is configured to become operable in response to the usage indicator being reduced by the adaptor.

9. The apparatus of claim 8, further comprising a plurality of reconditioned surgical instruments, wherein each of the plurality of reconditioned surgical instruments respectively stores an instrument identifiers thereon and a reconditioned device usage data, wherein the adaptor is configured to store a set of instrument identifiers, and wherein the adaptor is configured to modify the respective reconditioned device usage data only when the respective instrument identifier is present in the set of instrument identifiers.

10. The apparatus of claim 9, wherein the adaptor is configured to modify the set of usage data on the memory and reduce the usage indicator of the set of usage data to allow the surgical instrument to be usable for one future procedure after use for the present procedure.

11. The apparatus of claim 9, wherein the adaptor is configured to modify the set of usage data on the memory and reduce the usage indicator of the set of usage data to allow the surgical instrument to be usable for an unlimited number of future procedures after use for the present procedure.

12. The apparatus of claim 9, wherein the adaptor is configured to:
   (i) modify the set of usage data on the memory and reduce the usage indicator of the set of usage data to reset the memory to a factory state,
   (ii) store an override counter indicating a number of surgical instrument memories that have been reset to the factory state, and
   (iii) allow a limited number of factory resets based on the override counter.

13. The apparatus of claim 9, wherein the adaptor is configured to:

(i) modify the set of usage data on the memory and reduce the usage indicator of the set of usage data to reset the memory to a factory state,
(ii) store a device mapping that uniquely identifies the surgical instrument, and
(iii) prevent modification of usage data on a memory of any surgical instrument that is already uniquely identified in the device mapping.

14. A method of providing a notification from a surgical instrument, comprising:
   (a) connecting the surgical instrument to a surgical generator;
   (b) at the surgical generator, receiving a set of usage data from a memory of the surgical instrument;
   (c) determining if the set of usage data indicates that the surgical instrument will become inoperable after being used for a present procedure;
   (d) receiving a signal indicating that the surgical instrument is no longer in use;
   (e) in response to a determination that the surgical instrument will become inoperable and the signal indicating that the surgical instrument is no longer in use, providing the notification that the surgical instrument is inoperable for subsequent uses; and
   (f) automatically activating a usability indicator on the surgical instrument to indicate that the surgical instrument is inoperable for subsequent uses.

15. The method of claim 14, further comprising:
   (a) displaying an acknowledgment prompt via a display with the notification that the surgical instrument is inoperable for subsequent uses; and
   (b) preventing further use of the surgical generator with any surgical instrument until a user interacts with the acknowledgement prompt.

16. The method of claim 15, wherein the signal indicating that the surgical instrument is no longer in use is caused by a loss of communication between the surgical generator and the surgical instrument as a result of:
   (i) the surgical generator being disconnected from the surgical instrument, or
   (ii) a loss of external power to the surgical generator.

17. The method of claim 14, wherein providing the notification further includes providing the notification via a display of the surgical generator that the surgical instrument is inoperable for subsequent uses, and wherein automatically activating the usability indicator further includes automatically activating the usability indicator on the surgical instrument to indicate that the surgical instrument is inoperable for subsequent uses when providing the notification via the display.

18. The method of claim 17, further comprising, after completion of the present procedure:
   (a) disposing of the surgical instrument if the usability indicator is activated; and
   (b) sterilizing the surgical instrument if the usability indicator is not activated.

19. The method of claim 17, wherein activating the usability indicator comprises activating a sound indicator of the surgical instrument to emit audible tones until an internal power source of the surgical instrument is expended.

20. The method of claim 17, wherein activating the usability indicator comprises activating a light indicator of the surgical instrument to emit light until an internal power source of the surgical instrument is expended.

* * * * *